(12) United States Patent
Gomes et al.

(10) Patent No.: US 6,440,373 B1
(45) Date of Patent: Aug. 27, 2002

(54) DEVICE FOR COLLECTING AND STORING SAMPLES

(75) Inventors: Francis Gomes, Jersey City; Mark Follman, Glen Rock; David Landsberger, Caldwell, all of NJ (US)

(73) Assignee: Bel-Art Products, Inc., Pequannock, NJ (US)

( * ) Notice: Subject to any disclaimer, the term of this patent is extended or adjusted under 35 U.S.C. 154(b) by 0 days.

(21) Appl. No.: 09/418,471

(22) Filed: Oct. 15, 1999

(51) Int. Cl.[7] .................................................. B01L 3/00
(52) U.S. Cl. ...................................... 422/102; 426/518
(58) Field of Search ........................ 426/518; 422/102; 294/1.3; 210/232; 73/864.91; 436/174

(56) References Cited

U.S. PATENT DOCUMENTS

| | | |
|---|---|---|
| 1,642,985 A | 9/1927 | Beebe |
| 2,592,192 A | 4/1952 | Sanford |
| 2,718,060 A | 9/1955 | Buck, Jr. |
| 2,770,135 A | 11/1956 | Parvin |
| 2,799,086 A | 7/1957 | Tupper |
| 3,001,404 A | 9/1961 | McDonnell, Jr. |
| 3,013,436 A | 12/1961 | Dailey |
| 3,049,014 A | 8/1962 | Aue |
| D253,869 S | 1/1980 | Wells |
| 4,735,905 A | 4/1988 | Parker |
| 4,859,610 A * | 8/1989 | Maggio ...................... 436/518 |
| D328,867 S | 8/1992 | Watt et al. |
| 5,149,506 A | 9/1992 | Skiba et al. |
| 5,347,865 A | 9/1994 | Mulry et al. |
| 5,431,884 A | 7/1995 | McDonough et al. |
| 5,440,942 A | 8/1995 | Hubbard |
| 5,624,554 A | 4/1997 | Faulkner et al. |

FOREIGN PATENT DOCUMENTS

CH          672873 A   *   1/1990   .................. 294/1.3

OTHER PUBLICATIONS

Bel–Art Products, Inc. Catalog 198 (pp. 381–413).

* cited by examiner

Primary Examiner—Jill Warden
Assistant Examiner—Brian J. Sines
(74) Attorney, Agent, or Firm—Lawrence G. Fridman

(57) ABSTRACT

A device for collecting and storing a sample from relatively hard or loose products includes a container having an open end and a sample collection unit. The sample collection unit has a cap adapted to close the container open end, a handle extending rearwardly from the cap, and a coring scoop extending forwardly from the cap. The coring scoop is sized to fit within the container when closed by the cap. The coring scoop includes a pair of spaced side walls that are integrally joined by a curved connecting wall with a center of curvature to form an open channel into which a sample is received during sample collection. The handle comprises first and second I-beams extending rearwardly from the cap and intersecting each other along a longitudinal axis that is coincident with the center of curvature to thereby form a plurality of torque arms that extend radially from the axis.

19 Claims, 6 Drawing Sheets

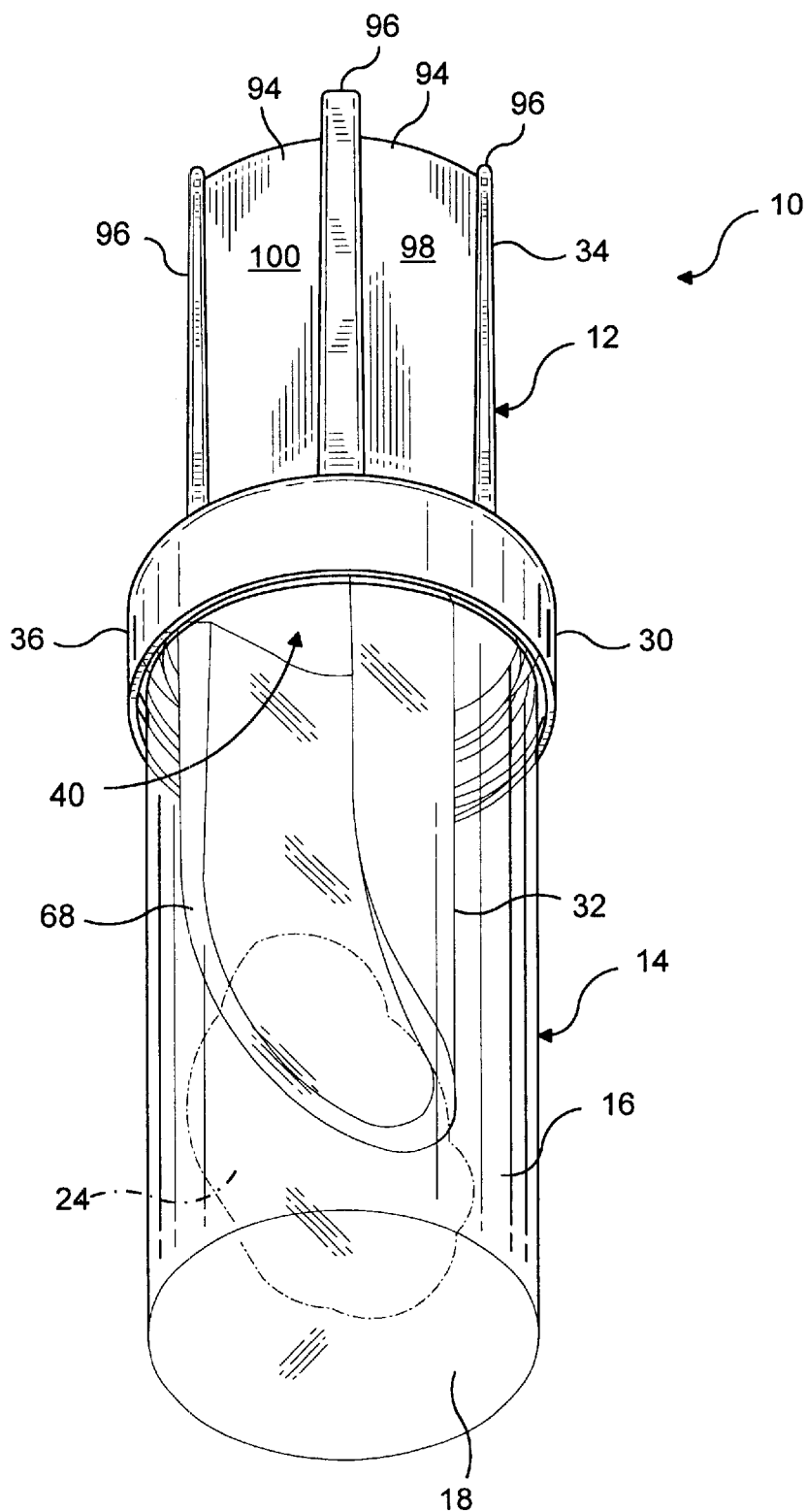
F I G. 2

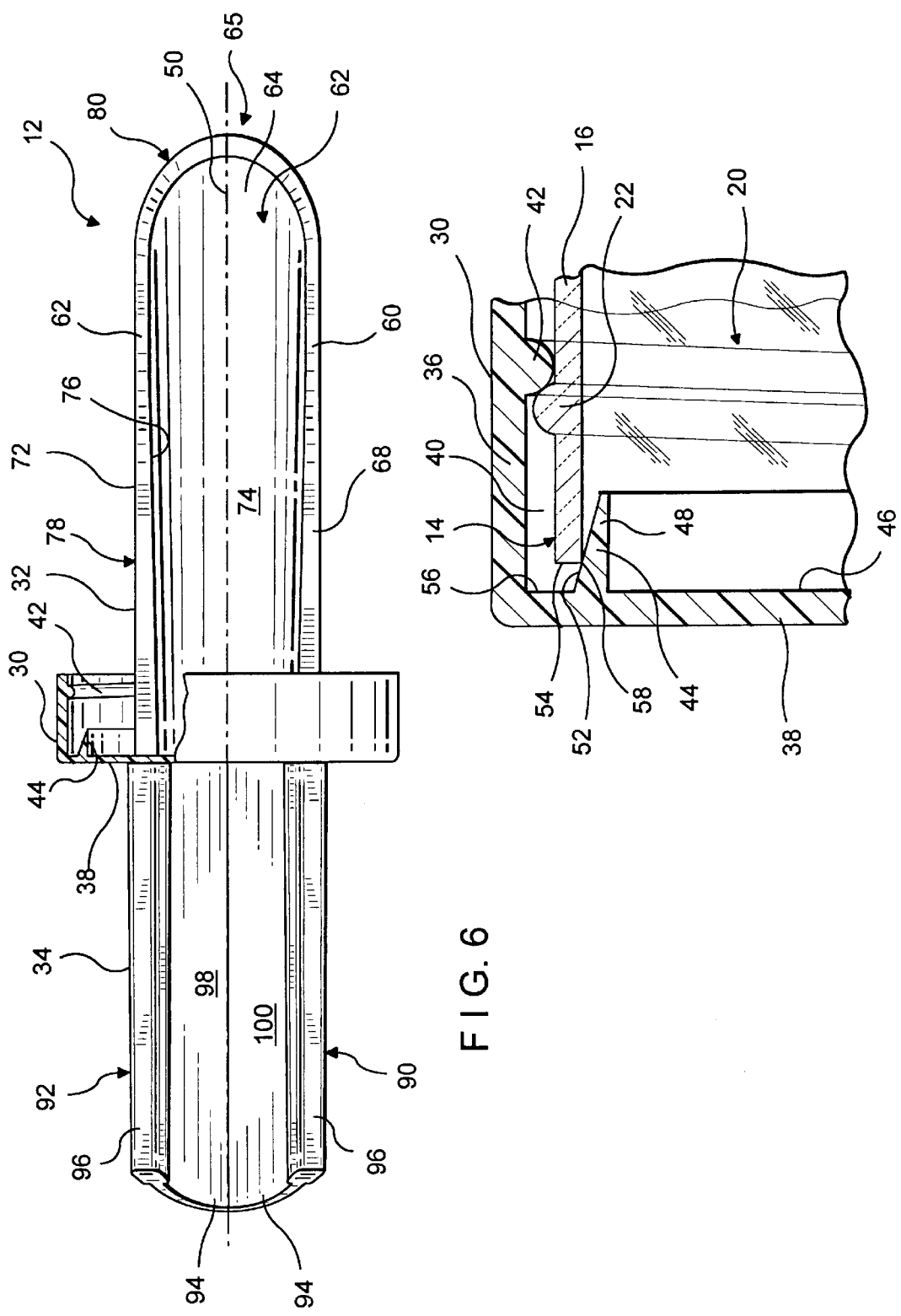

DEVICE FOR COLLECTING AND STORING SAMPLES

BACKGROUND OF THE INVENTION

1. Field of the Invention

This invention relates to collecting and transporting samples, and more particularly to a device for collecting and transporting solid and semi-solid samples in food and other industries.

2. Description of the Related Art

The dairy industry typically samples finished products such as hard and soft ice cream, cheese and so on, as well as loose ingredients such as cookies, nuts, chips, fudge, etc., on a daily basis for assuring that quality standards are met on a continual basis. Depending on the size of the manufacturing facility and the number of product offerings, the number of samples taken can easily reach the hundreds each day.

The collection of relatively hard food samples typically involves food collection systems with a corer or scoop that separates a relatively small sample from a main body of the product and a container for shipping the sample to a laboratory for analysis. Separation of the food sample with a corer involves inserting the corer into the main body of the product then rotating the corer, while separation with the scoop involves only longitudinal motion of the scoop with respect to the bulk or main body. Typically, the corer is formed with at least one flat surface to break the food sample from the main body during rotation. Design of the corer including an important flat surface thereof together with the hardness of the material often determine the amount of torque required to separate the food sample. For products such as hard ice cream or cheese, the required torque is relatively high and therefore demands a strenuous effort by the individual taking the sample.

Moreover, the collection of relatively hard samples requires a corer, while the collection of relatively soft or loose samples requires a scoop, thereby adding to the overall cost of quality control.

In addition, the corers, scoops and containers are typically reusable and are therefore constructed of materials that can be sterilized, such as stainless steel for the corers or scoops, and heat-resistant glass for the containers. The material and manufacturing costs of the corers, scoops and containers utilizing such materials is relatively high. Furthermore, the time and resources involved in returning such food collection systems from the laboratory, as well as the cleaning and sterilizing processes prior to taking samples greatly increases the costs associated with quality control, especially when hundreds of samples are taken each day.

SUMMARY OF THE INVENTION

It is therefore an object of the present invention to provide an arrangement for taking samples of products and storing such samples without the threat of contamination.

It is a further object of the invention to provide a device for collecting and storing a sample from a product that has a combination corer and scoop to thereby collect samples that are hard, soft, and loose with a single device; the device capable of withstanding a relatively high torque.

It is an even further object of the invention to provide a device for collecting and storing a sample from a product that is relatively inexpensive to manufacture and easy to use.

According to the invention, a device for collecting and storing a sample from a product comprises a container having an open end and a sample collection unit. The sample collection unit has a cap that is adapted to close the container open end, a handle that extends rearwardly from the cap, and a coring scoop that extends forwardly from the cap and being sized to fit within the container when the container is closed by the cap. The coring scoop includes a pair of spaced side wall portions that are integrally joined by a curved connecting wall portion with a center of curvature to form an open channel into which a sample is received during sample collection. Preferably, the side wall portions are substantially straight. With this arrangement, rotation of the sample collection unit about the center of curvature in the product forms a sample of the product in the open channel with the side wall portions pushing surrounding product away from the sample.

According to a further embodiment of the invention, a device for collecting and storing a sample from a product comprises a container having an open end and a sample collection unit. The sample collection unit has a cap that is adapted to close the container open end, a handle that extends rearwardly from the cap, and a coring scoop that extends forwardly from the cap and being sized to fit within the container when the container is closed by the cap. The handle comprises first and second beams that extend rearwardly from the cap and intersect each other along a longitudinal centerline to thereby form a plurality of torque arms that extend radially from the centerline. With this arrangement, rotation of the sample collection unit in the product about the longitudinal centerline forms a sample of the product in the coring scoop.

Other objects and advantages of the invention will become apparent upon reading the following detailed description and appended claims, and upon reference to the accompanying drawings.

BRIEF DESCRIPTION OF THE DRAWINGS

The preferred embodiments of the present invention will hereinafter be described in conjunction with the appended drawings, wherein like designations denote like elements, and wherein:

FIG. 2 is an isometric assembly view of the sample collection and storage device of FIG. 1;

FIG. 6 is a top plan view of the sample collection unit with the cap portion in partial cross section;

FIG. 8. is an enlarged cross sectional view of a portion of the assembled sample collection and storage device.

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope of the invention. The invention will now be described with additional specificity and detail through the accompanying drawings.

DETAILED DESCRIPTION OF THE PREFERRED EMBODIMENTS

Figure 1:
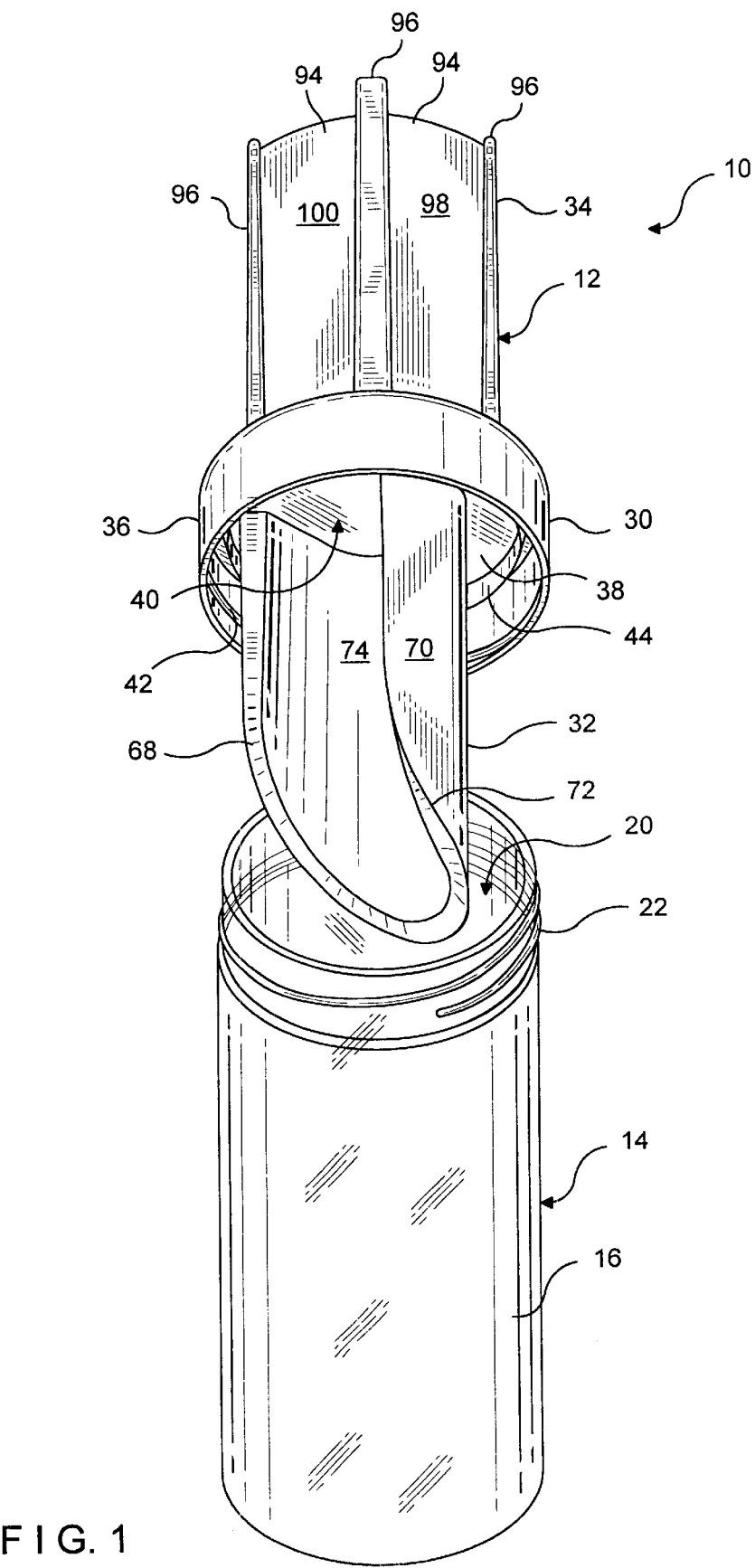
FIG. 1 is an isometric exploded view of a sample collection and storage device according to the invention.
Figure 3:
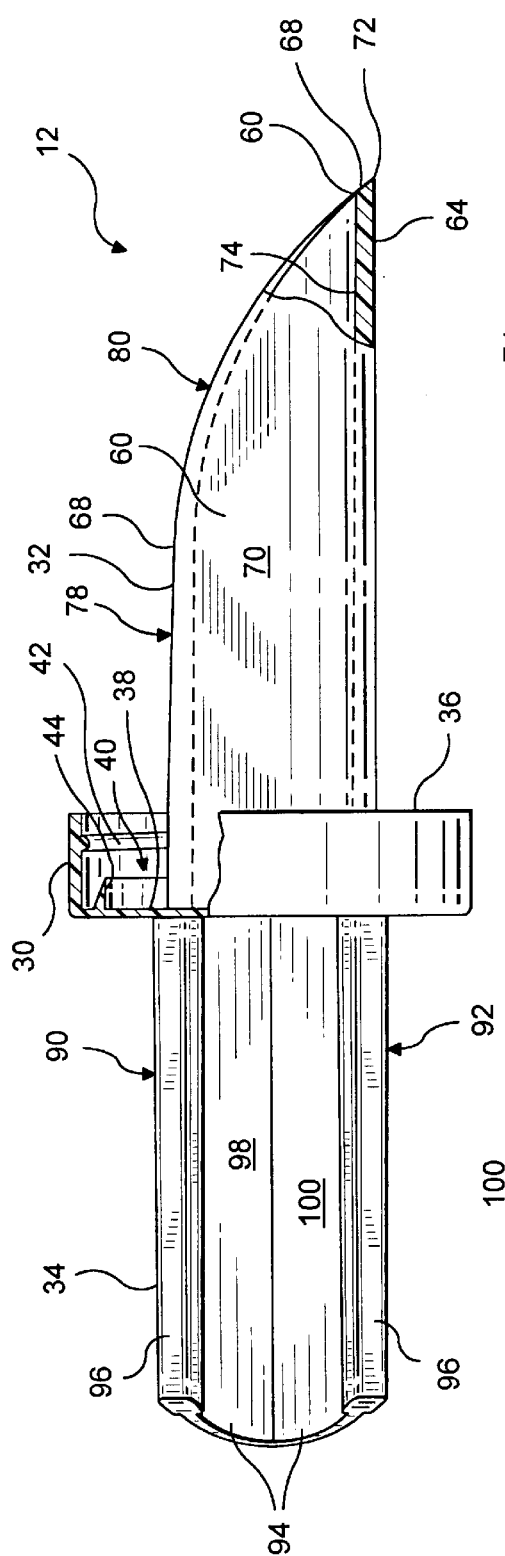
FIG. 3 is a side elevational view of a sample collection unit of the sample collection and storage device with cap and coring scoop portions in partial cross section to illustrate further details of the invention.

Referring now to the drawings in general, and to FIGS. 1 and 2 in particular, a sample collection and storage device 10 according to the invention comprises a sample collection unit 12 and a storage unit or vial 14.

The vial 14 is preferably of a substantially cylindrical configuration and includes a continuous side wall 16 that is integrally formed with a bottom wall 18 to form a hollow interior 20. It should be noted, however, that any conventional configuration of the vial is within the scope of the invention. Outer threads 22 are formed in the continuous side wall 16 at an upper end thereof. The vial 14 is preferably constructed of a transparent plastic material, such as high-impact polystyrene (HIPS) or other material that can be gamma irradiated for sterilization prior to receiving a sample 24 (shown in phantom line in FIGS. 2 and 9). Although a transparent material is preferred for viewing the sample within the vial 14, it is to be understood that translucent or opaque materials may be alternatively used, depending on the particular requirements of the sample and the requirements associated with sample testing.

With additional reference to FIGS. 3 to 7, the sample collection unit 12 includes a cap 30, a coring scoop 32 extending forwardly from the cap, and a handle 34 extending rearwardly from the cap. The cap 30 is preferably substantially cylindrical and includes a continuous side wall 36 that is integrally formed with a separating wall 38 to form a hollow interior 40. Inner threads 42 are formed in the interior area of the continuous side wall 36 which are adapted to mate with the outer threads 22 of the vial 14 when the cap and the vial are engaged.

As shown most clearly in FIG. 8, in one embodiment of the invention, an annular sealing ring 44 is formed on an inner surface 46 of the separating wall 38 and projects outwardly therefrom. The sealing ring 44 has an inner surface 48 that is generally parallel with a longitudinal axis 50 (See FIG. 6) of the sample collection unit 12 and an outer surface 52 that slopes generally toward the longitudinal axis. When the cap 30 is installed on the vial 14, the outer surface 52 of the sealing ring 44 and an inner edge 58 of an upper rim 54 of the vial are in mutual engagement for sealing the hollow interior 20 of the vial against the ingress of contaminants and the egress of a sample that may be in the vial. The sloped nature of the outer surface 52 assures a positive seal between the cap and vial despite relatively large tolerance variations that may occur during manufacture of the cap and vial. With less stringent tolerance requirements, manufacturing costs can be further reduced. If desired, an annular gasket (not shown) constructed of elastomeric material or the like can be inserted into a space 56 between the wall 36 and the sealing ring 44 to contact and seal against the rim 54.

Figure 5:
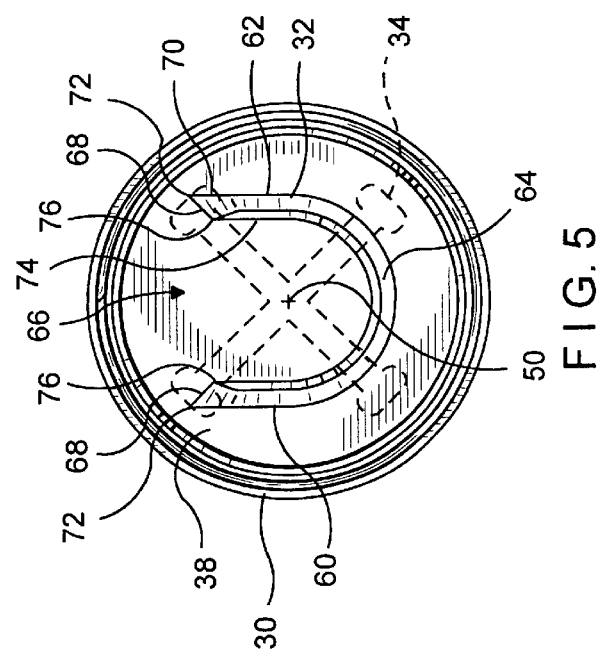
FIG. 5 is a front view of the sample collection unit.

Referring again to FIGS. 3 to 7, the coring scoop 32 includes a pair of spaced side wall portions 60, 62 that are integrally joined by a connecting wall portion 64 to form an open channel 66 into which the sample is received during sample collection. A rear end of the wall portions are joined to the separating wall 38 of the cap 30. As shown, the side wall portions 60, 62 are substantially straight and extend substantially parallel to each other, while the connecting wall portion 64 is curved. In an alternative arrangement, only one side wall is straight and the side wall portions 60, 62 extend in a non-parallel fashion. In one embodiment of the invention, the center of curvature of the connecting wall portion 64 is coincident with the longitudinal axis 50. A front end of the connecting wall portion 64 includes an arcuate section 65 that curves generally downwardly. The wall portions 60, 62 and 64 are arranged to form a continuous front surface 68 that intersects a continuous outer surface 70 of the coring scoop at an outer cutting edge 72. A continuous inner surface 74 of the coring scoop intersects the continuous front surface 68 at an inner edge 76. At each side wall, the front engaging surface 68 is formed with a first straight section 78 that extends from the separating wall 38 substantially parallel to the longitudinal axis 50, and a second curved section 80 that extends generally downwardly and forwardly from the first section 70 to the connecting wall portion 64. As best illustrated in FIGS. 5 and 9, the front surface 68 preferably slopes inwardly along its length from the cutting edge 72 to the inner edge 76.

Figure 4:
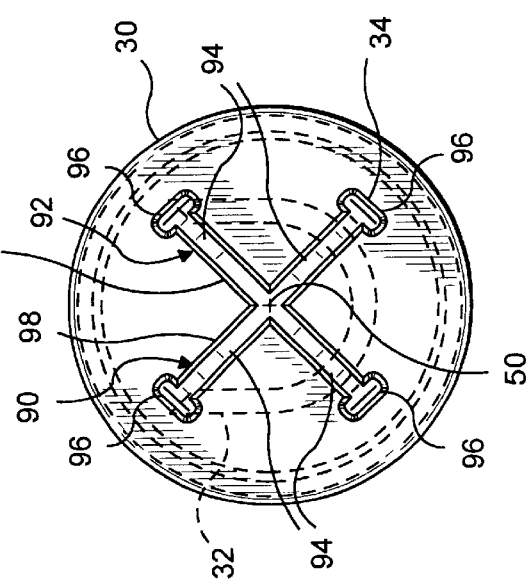
FIG. 4 is a rear view of the sample collection unit.
Figure 7:
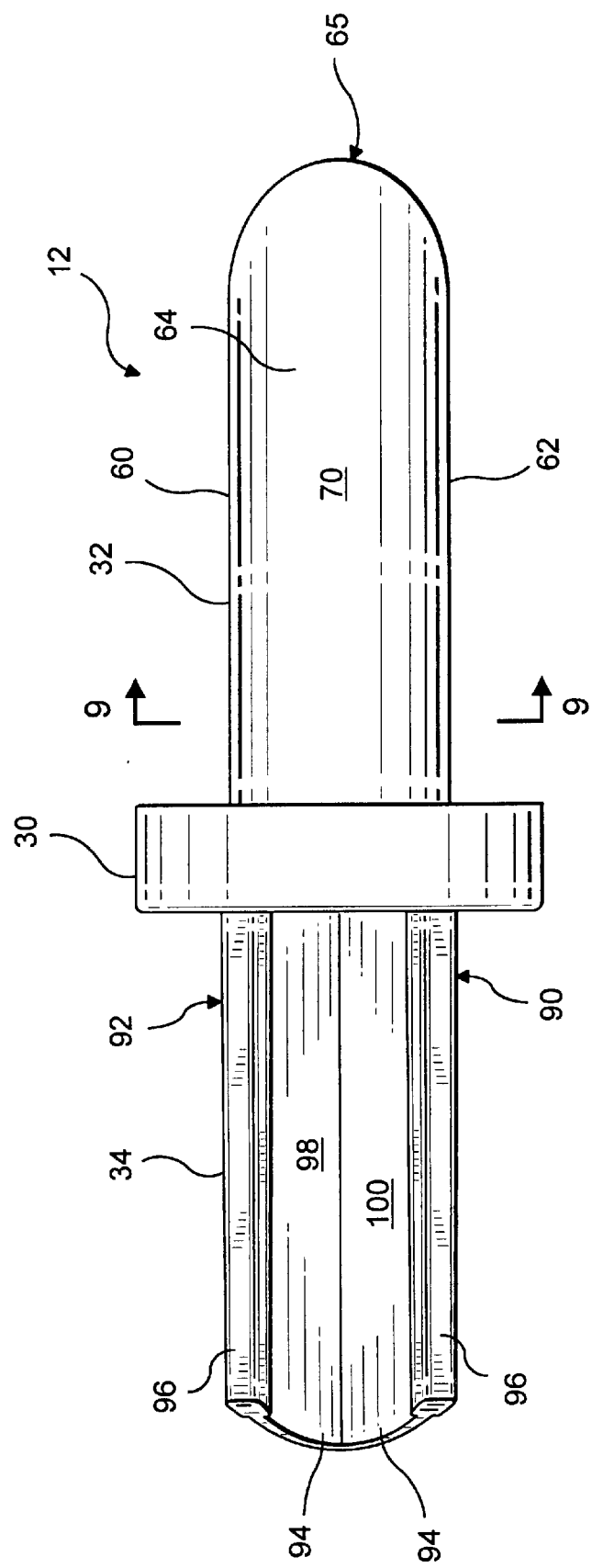
FIG. 7 is a bottom plan view of the sample collection unit.

As shown most clearly in FIG. 4, the handle 34 includes a first I-beam 90 that intersects a second I-beam 92 along the longitudinal axis 50 to form four torque arms 94 that extend radially from the axis 50 at about 90 degree segments and rearwardly from the separating wall 38 of the cap 30. Preferably, the torque arms 94 are equal in radial length and in height. A flange 96 is formed at the outer upright edge of each torque arm 94 and extends longitudinally along its length. Each torque arm 94 includes a pair of opposed, flat surfaces 98, 100 which can be adapted to receive a label (not shown) for identifying the contents of the vial 14. Although the handle with two I-beams has been illustrated and discussed hereinabove, a handle with any reasonable number of such I-beams, such as three or four I-beams is also contemplated.

The sample collection unit 12 is preferably molded of a plastic material, such as high-impact styrene, that can be gamma irradiated for sterilization and that exhibits good stiffness and strength to resist forces during sampling. The coring scoop 32, cap 30 and handle 34 are preferably integrally molded into a unitary structure during the manufacturing process. However, each part may be formed separately and joined together through ultrasonic welding, adhesive, or other known joining techniques. If desired, the entire collection unit 12 or the handle 34 may be colored during manufacture to provide color coding for different types of samples and/or laboratory analyses.

Figure 9:
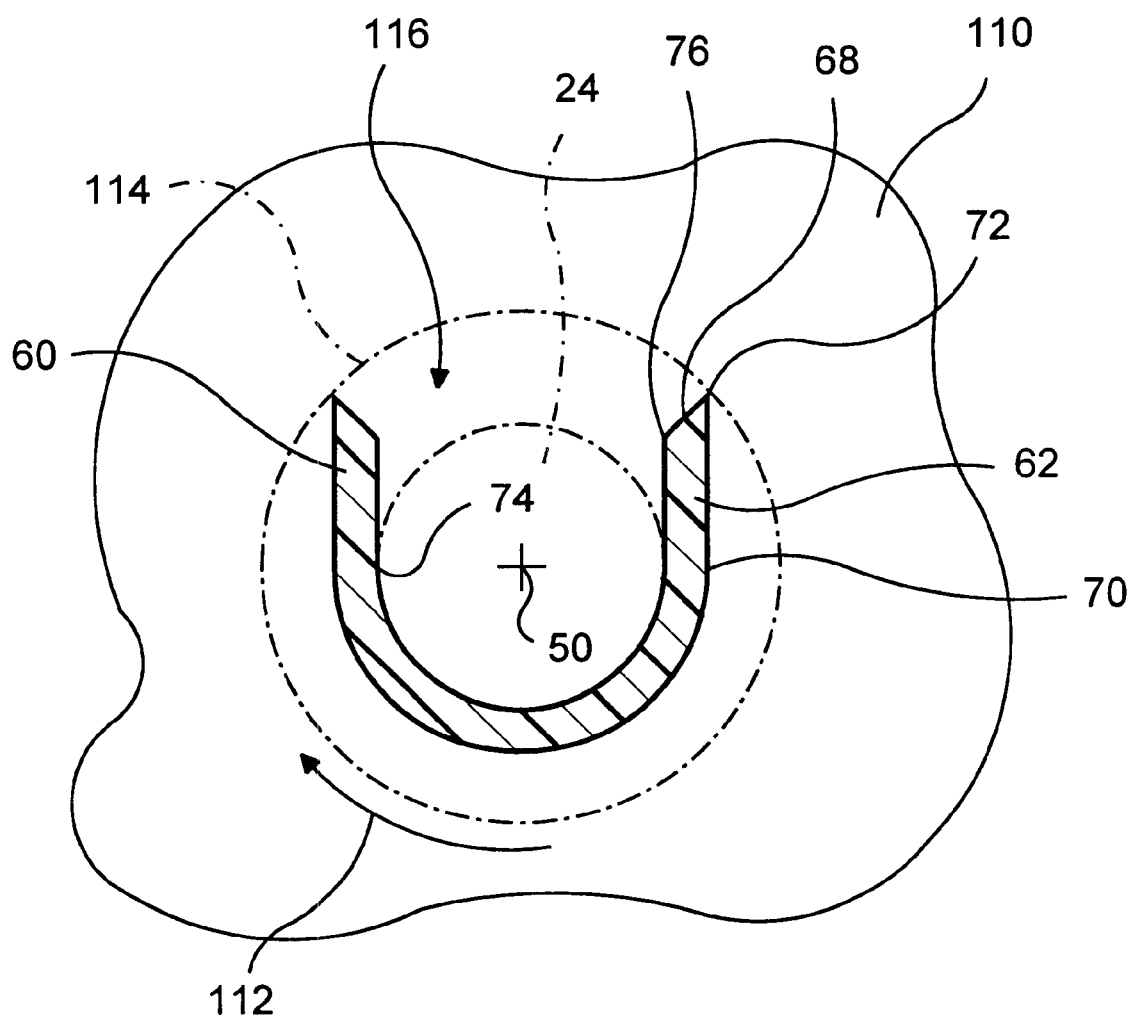
FIG. 9 is an enlarged cross sectional view of the sample collection unit taken along line 9—9 of FIG. 7 and showing the unit in operation for obtaining a sample.

In use, and with further reference to FIG. 9, the sample collection unit 12 is inserted into a solid or semi-solid product 110 such as cheese, ice cream, or other product, with the longitudinal axis 50 oriented generally normal to a surface of the product. The lower arcuate section 65 together with the curved section 80, cutting edge 72, and angled surface 68 simplifies entry of coring scoop 32 into the product. Once the coring scoop 32 is inserted to a predetermined depth in the product, the collection unit 12 is rotated about the longitudinal axis 50. This occurs when the user grasps the handle 34 and presses against the flat surfaces 98 or 100 (depending on the direction of rotation) and flanges 96 of the torque arms 94 with the inner surface of the hand and/or the thumb and fingers. The flanges 96 assure a tight grip on the handle while rotating and, together with the torque arms, provide a robust grip of the handle regardless of hand size. This is especially important when obtaining samples from relatively hard products are obtained. During rotation of the collection unit 12 in the direction as represented by arrow 112 in FIG. 9, the inner surface 74 of the coring scoop forms a generally cylindrical core sample 24. Simultaneously, the cutting edge 72 together with the substantially straight wall portion 62 cuts through the product 110 and pushes excess product away from the core sample 24 in a circular path 114. This motion creates a space 116 between the core sample 24 and the remainder of the product 110. Depending on the type of product being sampled, the core sample 24 should be separated from the remainder of the product during rotation due to the forces acting on the straight wall portions 60, 62 from the remaining product. If separation does not occur, the collection unit 12 can be tilted in a remaining space 116 to break the core sample from the product. Once the core sample is separated from the product, the vial 14 is screwed onto the cap to seal the coring scoop and the sample in the vial for storage and transportation as previously described. The position of the cap 30 with respect to the handle 34 and coring scoop 32 minimizes the risk of inadvertent contact between the user's hand and the sample, and thus minimizes the possibility of sample contamination.

It is to be understood that the terms upward, downward, upper, lower, forward, rearward, inner, outer, and their respective derivatives as used throughout the specification refer to relative, rather than absolute orientations or positions.

While the invention has been taught with specific reference to the above-described embodiments, those skilled in the art will recognize that changes can be made in form and detail without departing from the spirit and the scope of the invention. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A device for collecting and storing a sample from a product, the device comprising:
    a container having an open end;
    a sample collection unit having a cap adapted for closing the container open end, a handle extending rearwardly from the cap, the handle comprising first and second beams extending rearwardly from the cap and intersecting each other at a junction to thereby form a plurality of torque arms extending radially from the junction, a coring scoop extending forwardly from the cap and being sized to fit within the container when the container is closed by the cap, the coring scoop including a pair of spaced side walls integrally joined by a curved connecting wall having a center of curvature to form an open channel adapted to receive a sample during sample collection, at least one said side wall being substantially straight, each said side wall together with the connecting wall forming a portion of the continuous front surface having a first straight section that extends substantially parallel to a longitudinal axis of the sample collection unit and a second curved section that extends from the first straight section to a free end of the coring scoop to thereby facilitate insertion of the coring scoop into the product;
    wherein the rotation of the sample collection unit about the center of curvature in the product forms a sample of the product in the open channel with the side wall portions pushing surrounding product away from the sample.

2. A device according to claim 1, wherein said cap includes a separating wall situated substantially perpendicular to the longitudinal axis, the side walls extend from the separating wall in a substantially parallel direction.

3. A device according to claim 1, wherein the sample collection unit is integrally formed of a plastic material.

4. A device according to claim 1, wherein the lower free end of the coring scoop includes an arcuate section that curves generally downwardly to thereby facilitate insertion of the coring scoop into the product.

5. A device according to claim 1, wherein the side walls together with the connecting wall form a continuous outer surface that intersects the continuous front surface at an outer cutting edge to thereby facilitate rotation of the coring scoop in the product.

6. A device according to claim 5, wherein the side wall together with the connecting wall form a continuous inner surface that intersects the continuous front surface at an inner edge.

7. A device according to claim 6, wherein the continuous front surface slopes toward the center of curvature from the outer cutting edge to the inner edge.

8. A device according to claim 1, wherein the junction between the first and second beams is coincident with the center of curvature of the separating wall portion to thereby faciliate rotating the coring scoop about the center of curvature.

9. A device according to claim 8, wherein the intersecting beams form four torque arms extending radially from the junction at approximately 90 degree segments.

10. A device according to claim 1, further comprising a flange formed along an outer upright edge of each said torque arm to thereby facilitate securely gripping the handle during rotation of the sample collection unit.

11. A device according to claim 1, wherein the cap is circular in shape and includes a separating wall connected to a continuous side wall, a central axis of the cap being coincident with the center of curvature.

12. A device according to claim 11, and further comprising an annular sealing ring extending outwardly from the separating wall of the cap, the annular sealing ring being adapted to engage the open end of the container to thereby seal the sample within the container.

13. A device according to claim 12, wherein the annular sealing ring includes a surface that slopes generally inwardly, the surface being adapted to engage an inner edge of the container opening to thereby seal the sample within the container.

14. A device for collecting and storing a sample from a product, the device comprising:
    a container having an open end;
    a sample collection unit having a cap adapted for closing the container open end, a handle extending rearwardly from the cap, and a coring scoop extending forwardly from the cap and being sized to fit within the container when the container is closed by the cap, the handle comprising first and second beams extending rearwardly from the cap and intersecting each other at a longitudinal centerline to thereby form a plurality of torque arms that extend radially from the centerline;
    wherein rotation of the sample collection unit about the longitudinal centerline in the product forms a sample of the product in the coring scoop.

15. A device according to claim 14, wherein the coring scoop includes a curved wall having a center of curvature that is coincident with the longitudinal axis to thereby facilitate rotating the sample collection unit around the longitudinal axis.

16. A device according to claim 14, wherein the intersecting beams form four torque arms extending radially from the longitudinal centerline at approximately 90 degree segments.

17. A device according to claim 14, and further comprising a flange formed along an outer upright edge of each torque arm to thereby facilitate gripping of the handle by a user during rotation of the sample collection unit.

18. A device according to claim 14, wherein the cap is substantially circular in shape and includes a separating wall connected to a continuous side wall, a central axis of the cap being coincident with the longitudinal axis of the handle.

19. A device according to claim 18, and further comprising an annular sealing ring extending downwardly from the separating wall of the cap, the annular sealing ring being adapted to engage the open end of the container to thereby seal the sample within the container.

* * * * *